(12) United States Patent
Price

(10) Patent No.: US 8,417,309 B2
(45) Date of Patent: Apr. 9, 2013

(54) MEDICAL SENSOR

(75) Inventor: Thomas Price, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 1146 days.

(21) Appl. No.: 12/241,251

(22) Filed: Sep. 30, 2008

(65) Prior Publication Data

US 2010/0081900 A1    Apr. 1, 2010

(51) Int. Cl.
*A61B 5/1455* (2006.01)
(52) U.S. Cl. .......................... 600/344; 600/323; 600/310
(58) Field of Classification Search ........... 600/309–344
See application file for complete search history.

(56) References Cited

U.S. PATENT DOCUMENTS

| | | |
|---|---|---|
| 3,638,640 A | 2/1972 | Shaw |
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |

(Continued)

FOREIGN PATENT DOCUMENTS

| | | |
|---|---|---|
| CN | 101080192 | 11/2007 |
| DE | 3516338 | 11/1986 |

(Continued)

OTHER PUBLICATIONS

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

(Continued)

*Primary Examiner* — Eric Winakur
*Assistant Examiner* — Marjan Fardanesh
(74) *Attorney, Agent, or Firm* — Fletcher Yoder

(57) ABSTRACT

The present disclosure generally relates to a medical sensor configured to attach to a patient's finger. According to embodiments, a sensor body is attached to a ring such that the sensor body is limited to contact with the patient's finger. The ring may have a fixed diameter or be adjustable. The ring may also include an indicator that facilitates the determination of whether the ring applies appropriate tension to the patient's finger. The sensor body may comprise a strip attached to the ring at two points or a hood that covers the distal end of the patient's finger. The sensor body may be coupled to the patient's finger with adhesives or securing flaps.

11 Claims, 6 Drawing Sheets

U.S. PATENT DOCUMENTS

| | | | |
|---|---|---|---|
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,903,507 A | 2/1990 | Gesensway |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,972,331 A | 11/1990 | Chance |
| 4,974,591 A | 12/1990 | Awazu et al. |
| 4,991,234 A * | 2/1991 | Greenberg ............... 2/170 |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,039 A | 8/1991 | Hattori et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp, Jr. et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,239,842 A | 8/1993 | Gesensway |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,412,956 A | 5/1995 | Levy |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,413,553 A * | 5/1995 | Downes ............... 602/21 |
| 5,417,207 A | 5/1995 | Young et al. |

| | | | | | | |
|---|---|---|---|---|---|---|
| 5,421,329 | A | 6/1995 | Casciani et al. | 5,687,719 | A | 11/1997 | Sato et al. |
| 5,425,360 | A | 6/1995 | Nelson | 5,687,722 | A | 11/1997 | Tien et al. |
| 5,425,362 | A | 6/1995 | Siker et al. | 5,692,503 | A | 12/1997 | Kuenstner |
| 5,427,093 | A | 6/1995 | Ogawa et al. | 5,692,505 | A | 12/1997 | Fouts |
| 5,429,128 | A | 7/1995 | Cadell et al. | 5,709,205 | A | 1/1998 | Bukta |
| 5,429,129 | A | 7/1995 | Lovejoy et al. | 5,713,355 | A | 2/1998 | Richardson et al. |
| 5,431,159 | A | 7/1995 | Baker et al. | 5,724,967 | A | 3/1998 | Venkatachalam |
| 5,431,170 | A | 7/1995 | Mathews | 5,727,547 | A | 3/1998 | Levinson et al. |
| 5,437,275 | A | 8/1995 | Amundsen et al. | 5,730,124 | A | 3/1998 | Yamauchi |
| 5,438,986 | A | 8/1995 | Disch et al. | 5,731,582 | A | 3/1998 | West |
| 5,448,991 | A | 9/1995 | Polson et al. | D393,830 | S | 4/1998 | Tobler et al. |
| 5,452,717 | A | 9/1995 | Branigan et al. | 5,743,260 | A | 4/1998 | Chung et al. |
| 5,465,714 | A | 11/1995 | Scheuing | 5,743,263 | A | 4/1998 | Baker, Jr. |
| 5,469,845 | A | 11/1995 | DeLonzor et al. | 5,746,206 | A | 5/1998 | Mannheimer |
| RE35,122 | E | 12/1995 | Corenman et al. | 5,746,697 | A | 5/1998 | Swedlow et al. |
| 5,482,034 | A | 1/1996 | Lewis et al. | 5,752,914 | A | 5/1998 | DeLonzor et al. |
| 5,482,036 | A | 1/1996 | Diab et al. | 5,755,226 | A | 5/1998 | Carim et al. |
| 5,483,646 | A | 1/1996 | Uchikoga | 5,758,644 | A | 6/1998 | Diab et al. |
| 5,485,847 | A | 1/1996 | Baker, Jr. | 5,760,910 | A | 6/1998 | Lepper, Jr. et al. |
| 5,490,505 | A | 2/1996 | Diab et al. | 5,766,125 | A | 6/1998 | Aoyagi et al. |
| 5,490,523 | A | 2/1996 | Isaacson et al. | 5,766,127 | A | 6/1998 | Pologe et al. |
| 5,491,299 | A | 2/1996 | Naylor et al. | 5,769,785 | A | 6/1998 | Diab et al. |
| 5,494,032 | A | 2/1996 | Robinson et al. | 5,772,587 | A | 6/1998 | Gratton et al. |
| 5,497,771 | A | 3/1996 | Rosenheimer | 5,774,213 | A | 6/1998 | Trebino et al. |
| 5,499,627 | A | 3/1996 | Steuer et al. | 5,776,058 | A | 7/1998 | Levinson et al. |
| 5,503,148 | A | 4/1996 | Pologe et al. | 5,776,059 | A | 7/1998 | Kaestle |
| 5,505,199 | A | 4/1996 | Kim | 5,779,630 | A | 7/1998 | Fein et al. |
| 5,507,286 | A | 4/1996 | Solenberger | 5,779,631 | A | 7/1998 | Chance |
| 5,517,988 | A | 5/1996 | Gerhard | 5,782,237 | A | 7/1998 | Casciani et al. |
| 5,520,177 | A | 5/1996 | Ogawa et al. | 5,782,756 | A | 7/1998 | Mannheimer |
| 5,521,851 | A | 5/1996 | Wei et al. | 5,782,757 | A | 7/1998 | Diab et al. |
| 5,522,388 | A | 6/1996 | Ishikawa et al. | 5,782,758 | A | 7/1998 | Ausec et al. |
| 5,524,617 | A | 6/1996 | Mannheimer | 5,786,592 | A | 7/1998 | Hök |
| 5,529,064 | A | 6/1996 | Rall et al. | 5,790,729 | A | 8/1998 | Pologe et al. |
| 5,533,507 | A | 7/1996 | Potratz et al. | 5,792,052 | A | 8/1998 | Isaacson et al. |
| 5,551,423 | A | 9/1996 | Sugiura | 5,795,292 | A | 8/1998 | Lewis et al. |
| 5,551,424 | A | 9/1996 | Morrison et al. | 5,797,841 | A | 8/1998 | DeLonzor et al. |
| 5,553,614 | A | 9/1996 | Chance | 5,800,348 | A | 9/1998 | Kaestle |
| 5,553,615 | A | 9/1996 | Carim et al. | 5,800,349 | A | 9/1998 | Isaacson et al. |
| 5,555,882 | A | 9/1996 | Richardson et al. | 5,803,910 | A | 9/1998 | Potratz |
| 5,558,096 | A | 9/1996 | Palatnik | 5,807,246 | A | 9/1998 | Sakaguchi et al. |
| 5,560,355 | A | 10/1996 | Merchant et al. | 5,807,247 | A | 9/1998 | Merchant et al. |
| 5,564,417 | A | 10/1996 | Chance | 5,807,248 | A | 9/1998 | Mills |
| 5,575,284 | A | 11/1996 | Athan et al. | 5,810,723 | A | 9/1998 | Aldrich |
| 5,575,285 | A | 11/1996 | Takanashi et al. | 5,810,724 | A | 9/1998 | Gronvall |
| 5,577,500 | A | 11/1996 | Potratz | 5,813,980 | A | 9/1998 | Levinson et al. |
| 5,582,169 | A | 12/1996 | Oda et al. | 5,817,008 | A | 10/1998 | Rafert et al. |
| 5,584,296 | A | 12/1996 | Cui et al. | 5,817,009 | A | 10/1998 | Rosenheimer et al. |
| 5,588,425 | A | 12/1996 | Sackner et al. | 5,817,010 | A | 10/1998 | Hibl |
| 5,588,427 | A | 12/1996 | Tien | 5,818,985 | A | 10/1998 | Merchant et al. |
| 5,590,652 | A | 1/1997 | Inai | 5,820,550 | A | 10/1998 | Polson et al. |
| 5,595,176 | A | 1/1997 | Yamaura | 5,823,950 | A | 10/1998 | Diab et al. |
| 5,596,986 | A | 1/1997 | Goldfarb | 5,823,952 | A | 10/1998 | Levinson et al. |
| 5,611,337 | A | 3/1997 | Bukta | 5,827,182 | A | 10/1998 | Raley et al. |
| 5,617,852 | A | 4/1997 | MacGregor | 5,830,135 | A | 11/1998 | Bosque et al. |
| 5,619,992 | A | 4/1997 | Guthrie et al. | 5,830,136 | A | 11/1998 | DeLonzor et al. |
| 5,626,140 | A | 5/1997 | Feldman et al. | 5,830,137 | A | 11/1998 | Scharf |
| 5,630,413 | A | 5/1997 | Thomas et al. | 5,830,139 | A | 11/1998 | Abreu |
| 5,632,272 | A | 5/1997 | Diab et al. | 5,831,598 | A | 11/1998 | Kauffert et al. |
| 5,632,273 | A | 5/1997 | Suzuki | 5,839,439 | A | 11/1998 | Nierlich et al. |
| 5,634,459 | A | 6/1997 | Gardosi | RE36,000 | E | 12/1998 | Swedlow et al. |
| 5,638,593 | A | 6/1997 | Gerhardt et al. | 5,842,979 | A | 12/1998 | Jarman et al. |
| 5,638,818 | A | 6/1997 | Diab et al. | 5,842,981 | A | 12/1998 | Larsen et al. |
| 5,645,059 | A | 7/1997 | Fein et al. | 5,842,982 | A | 12/1998 | Mannheimer |
| 5,645,060 | A | 7/1997 | Yorkey et al. | 5,846,190 | A | 12/1998 | Woehrle |
| 5,645,440 | A | 7/1997 | Tobler et al. | 5,851,178 | A | 12/1998 | Aronow |
| 5,660,567 | A | 8/1997 | Nierlich et al. | 5,851,179 | A | 12/1998 | Ritson et al. |
| 5,662,105 | A | 9/1997 | Tien | 5,853,364 | A | 12/1998 | Baker, Jr. et al. |
| 5,662,106 | A | 9/1997 | Swedlow et al. | 5,860,919 | A | 1/1999 | Kiani-Azarbayjany et al. |
| 5,666,952 | A | 9/1997 | Fuse et al. | 5,865,736 | A | 2/1999 | Baker, Jr. et al. |
| 5,671,529 | A | 9/1997 | Nelson | 5,871,442 | A | 2/1999 | Madarasz et al. |
| 5,673,692 | A | 10/1997 | Schulze et al. | 5,873,821 | A | 2/1999 | Chance et al. |
| 5,673,693 | A | 10/1997 | Solenberger | 5,879,294 | A | 3/1999 | Anderson et al. |
| 5,676,139 | A | 10/1997 | Goldberger et al. | 5,885,213 | A | 3/1999 | Richardson et al. |
| 5,676,141 | A | 10/1997 | Hollub | 5,890,929 | A | 4/1999 | Mills et al. |
| 5,678,544 | A | 10/1997 | DeLonzor et al. | 5,891,021 | A | 4/1999 | Dillon et al. |
| 5,680,857 | A | 10/1997 | Pelikan et al. | 5,891,022 | A | 4/1999 | Pologe |
| 5,685,299 | A | 11/1997 | Diab et al. | 5,891,024 | A | 4/1999 | Jarman et al. |
| 5,685,301 | A | 11/1997 | Klomhaus | 5,891,025 | A | 4/1999 | Buschmann et al. |

| Patent | Date | Inventor |
|---|---|---|
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,120,460 A | 9/2000 | Abreu |
| 6,122,535 A | 9/2000 | Kaestle et al. |
| 6,133,994 A | 10/2000 | Mathews et al. |
| 6,134,460 A | 10/2000 | Chance |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllerman et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,312,393 B1 | 11/2001 | Abreu |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |

| | | |
|---|---|---|
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,415,236 B2 | 7/2002 | Kobayashi et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,487,439 B1 | 11/2002 | Skladnev et al. |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,544,193 B2 | 4/2003 | Abreu |
| 6,546,267 B1 | 4/2003 | Sugiura et al. |
| 6,549,795 B1 | 4/2003 | Chance |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,042 B1 | 9/2003 | Powell |
| 6,618,602 B2 | 9/2003 | Levin et al. |
| 6,622,034 B1 | 9/2003 | Gorski et al. |
| 6,622,095 B2 | 9/2003 | Kobayashi et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,030 B2 | 12/2003 | Khalil et al. |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,690,958 B1 | 2/2004 | Walker et al. |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,048 B1 | 3/2004 | Chance |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,245 B1 | 3/2004 | Ono |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B2 | 4/2004 | Kästle |
| 6,725,075 B2 | 4/2004 | Al-Ali |
| 6,731,274 B2 | 5/2004 | Powell |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |

| Patent No. | Date | Inventor(s) |
|---|---|---|
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,785,568 B2 | 8/2004 | Chance |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,053 B2 | 2/2005 | Daalmans et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,889,153 B2 | 5/2005 | Dietiker |
| 6,898,451 B2 | 5/2005 | Wuori |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,780 B2 | 9/2005 | Scharf |
| 6,947,781 B2 | 9/2005 | Asada et al. |
| 6,949,081 B1 | 9/2005 | Chance |
| 6,950,687 B2 | 9/2005 | Al-Ali |
| 6,961,598 B2 | 11/2005 | Diab |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,030,749 B2 | 4/2006 | Al-Ali |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boas et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,162,306 B2 | 1/2007 | Caby et al. |
| 7,190,987 B2 | 3/2007 | Lindekugel et al. |
| 7,198,778 B2 | 4/2007 | Achilefu et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,236,881 B2 | 6/2007 | Schmitt et al. |
| 7,245,953 B1 | 7/2007 | Parker |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,373,193 B2 | 5/2008 | Al-Ali et al. |
| 2001/0005773 A1 | 6/2001 | Larsen et al. |
| 2001/0020122 A1 | 9/2001 | Steuer et al. |
| 2001/0021803 A1 | 9/2001 | Blank et al. |
| 2001/0039376 A1 | 11/2001 | Steuer et al. |
| 2001/0044700 A1 | 11/2001 | Kobayashi et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |
| 2002/0035318 A1 | 3/2002 | Mannheimer et al. |
| 2002/0038078 A1 | 3/2002 | Ito |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0068859 A1 | 6/2002 | Knopp |
| 2002/0111748 A1 | 8/2002 | Kobayashi et al. |
| 2002/0128544 A1 | 9/2002 | Diab et al. |
| 2002/0133067 A1 | 9/2002 | Jackson, III |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2002/0198443 A1 | 12/2002 | Ting |
| 2003/0018243 A1 | 1/2003 | Gerhardt et al. |
| 2003/0023140 A1 | 1/2003 | Chance |
| 2003/0036690 A1 | 2/2003 | Geddes et al. |
| 2003/0045785 A1 | 3/2003 | Diab et al. |
| 2003/0055324 A1 | 3/2003 | Wasserman |
| 2003/0060693 A1 | 3/2003 | Monfre et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |

| | | | | | | |
|---|---|---|---|---|---|---|
| 2003/0132495 A1 | 7/2003 | Mills et al. | | 2004/0267103 A1 | 12/2004 | Li et al. |
| 2003/0135099 A1 | 7/2003 | Al-Ali | | 2004/0267104 A1 | 12/2004 | Hannula et al. |
| 2003/0139687 A1 | 7/2003 | Abreu | | 2004/0267140 A1 | 12/2004 | Ito et al. |
| 2003/0144584 A1 | 7/2003 | Mendelson | | 2005/0004479 A1 | 1/2005 | Townsend et al. |
| 2003/0162414 A1 | 8/2003 | Schulz et al. | | 2005/0010092 A1 | 1/2005 | Weber et al. |
| 2003/0171662 A1 | 9/2003 | O'Connor et al. | | 2005/0020887 A1 | 1/2005 | Goldberg |
| 2003/0176776 A1 | 9/2003 | Huiku | | 2005/0020894 A1 | 1/2005 | Norris et al. |
| 2003/0181799 A1 | 9/2003 | Lindekugel et al. | | 2005/0033128 A1 | 2/2005 | Ali et al. |
| 2003/0187337 A1 | 10/2003 | Tarassenko et al. | | 2005/0033129 A1 | 2/2005 | Edgar, Jr. et al. |
| 2003/0195402 A1 | 10/2003 | Fein et al. | | 2005/0043599 A1 | 2/2005 | O'Mara |
| 2003/0197679 A1 | 10/2003 | Ali et al. | | 2005/0043600 A1 | 2/2005 | Diab et al. |
| 2003/0212316 A1 | 11/2003 | Leiden et al. | | 2005/0049470 A1 | 3/2005 | Terry |
| 2003/0220548 A1 | 11/2003 | Schmitt | | 2005/0049471 A1 | 3/2005 | Aceti |
| 2003/0220576 A1 | 11/2003 | Diab | | 2005/0075550 A1 | 4/2005 | Lindekugel |
| 2003/0225323 A1 | 12/2003 | Kiani et al. | | 2005/0080323 A1 | 4/2005 | Kato |
| 2003/0225337 A1 | 12/2003 | Scharf et al. | | 2005/0101850 A1 | 5/2005 | Parker |
| 2003/0236452 A1 | 12/2003 | Melker et al. | | 2005/0113651 A1 | 5/2005 | Wood et al. |
| 2003/0236647 A1 | 12/2003 | Yoon et al. | | 2005/0113656 A1 | 5/2005 | Chance |
| 2004/0006261 A1 | 1/2004 | Swedlow et al. | | 2005/0168722 A1 | 8/2005 | Forstner et al. |
| 2004/0010188 A1 | 1/2004 | Wasserman et al. | | 2005/0177034 A1 | 8/2005 | Beaumont |
| 2004/0024297 A1 | 2/2004 | Chen et al. | | 2005/0192488 A1 | 9/2005 | Bryenton et al. |
| 2004/0024326 A1 | 2/2004 | Yeo et al. | | 2005/0197548 A1 | 9/2005 | Dietiker |
| 2004/0034293 A1 | 2/2004 | Kimball | | 2005/0203357 A1 | 9/2005 | Debreczeny et al. |
| 2004/0039272 A1 | 2/2004 | Abdul-Hafiz et al. | | 2005/0228248 A1 | 10/2005 | Dietiker |
| 2004/0039273 A1 | 2/2004 | Terry | | 2005/0267346 A1 | 12/2005 | Faber et al. |
| 2004/0054269 A1 | 3/2004 | Rantala et al. | | 2005/0277819 A1 | 12/2005 | Kiani et al. |
| 2004/0054270 A1 | 3/2004 | Pewzner et al. | | 2005/0283059 A1 | 12/2005 | Iyer et al. |
| 2004/0054291 A1 | 3/2004 | Schulz et al. | | 2006/0009688 A1 | 1/2006 | Lamego et al. |
| 2004/0059209 A1 | 3/2004 | Al-Ali et al. | | 2006/0015021 A1 | 1/2006 | Cheng |
| 2004/0059210 A1 | 3/2004 | Stetson | | 2006/0020181 A1 | 1/2006 | Schmitt |
| 2004/0064020 A1 | 4/2004 | Diab et al. | | 2006/0030763 A1 | 2/2006 | Mannheimer et al. |
| 2004/0068164 A1 | 4/2004 | Diab et al. | | 2006/0052680 A1 | 3/2006 | Diab |
| 2004/0087846 A1 | 5/2004 | Wasserman | | 2006/0058594 A1 | 3/2006 | Ishizuka et al. |
| 2004/0092805 A1 | 5/2004 | Yarita | | 2006/0058683 A1 | 3/2006 | Chance |
| 2004/0097797 A1 | 5/2004 | Porges et al. | | 2006/0064024 A1 | 3/2006 | Schnall |
| 2004/0098009 A1 | 5/2004 | Boecker et al. | | 2006/0069319 A1 | 3/2006 | Elhag et al. |
| 2004/0107065 A1 | 6/2004 | Al-Ali et al. | | 2006/0079794 A1 | 4/2006 | Liu et al. |
| 2004/0116788 A1 | 6/2004 | Chernoguz et al. | | 2006/0084852 A1 | 4/2006 | Mason et al. |
| 2004/0116789 A1 | 6/2004 | Boaz et al. | | 2006/0089547 A1 | 4/2006 | Sarussi |
| 2004/0117891 A1 | 6/2004 | Hannula et al. | | 2006/0106294 A1 | 5/2006 | Maser et al. |
| 2004/0122300 A1 | 6/2004 | Boas et al. | | 2006/0195028 A1 | 8/2006 | Hannula et al. |
| 2004/0122302 A1 | 6/2004 | Mason et al. | | 2006/0224058 A1 | 10/2006 | Mannheimer |
| 2004/0127779 A1 | 7/2004 | Steuer et al. | | 2006/0247501 A1 | 11/2006 | Ali |
| 2004/0133087 A1 | 7/2004 | Ali et al. | | 2006/0253010 A1 | 11/2006 | Brady et al. |
| 2004/0133088 A1 | 7/2004 | Al-Ali et al. | | 2006/0258921 A1 | 11/2006 | Addison et al. |
| 2004/0138538 A1 | 7/2004 | Stetson | | 2007/0027376 A1 | 2/2007 | Todokoro et al. |
| 2004/0138540 A1 | 7/2004 | Baker, Jr. et al. | | 2007/0032710 A1 | 2/2007 | Raridan et al. |
| 2004/0143172 A1 | 7/2004 | Fudge et al. | | 2007/0032712 A1 | 2/2007 | Raridan et al. |
| 2004/0147821 A1 | 7/2004 | Al-Ali et al. | | 2007/0032715 A1 | 2/2007 | Eghbal et al. |
| 2004/0147822 A1 | 7/2004 | Al-Ali et al. | | 2007/0073116 A1 | 3/2007 | Kiani et al. |
| 2004/0147823 A1 | 7/2004 | Kiani et al. | | 2007/0073126 A1 | 3/2007 | Raridan, Jr. |
| 2004/0147824 A1 | 7/2004 | Diab et al. | | 2007/0106132 A1 | 5/2007 | Elhag et al. |
| 2004/0152965 A1 | 8/2004 | Diab et al. | | 2007/0244377 A1 | 10/2007 | Cozad et al. |
| 2004/0158134 A1 | 8/2004 | Diab et al. | | 2007/0287898 A1 | 12/2007 | Lee et al. |
| 2004/0158135 A1 | 8/2004 | Baker, Jr. et al. | | 2008/0009691 A1 | 1/2008 | Parker |
| 2004/0162472 A1 | 8/2004 | Berson et al. | | 2008/0058622 A1* | 3/2008 | Baker .......................... 600/344 |
| 2004/0171920 A1 | 9/2004 | Mannheimer et al. | | 2008/0076980 A1 | 3/2008 | Hoarau |
| 2004/0171948 A1 | 9/2004 | Terry | | 2008/0076981 A1 | 3/2008 | Hoarau |
| 2004/0176670 A1 | 9/2004 | Takamura et al. | | 2008/0076994 A1 | 3/2008 | Hoarau |
| 2004/0176671 A1 | 9/2004 | Fine et al. | | 2008/0076995 A1 | 3/2008 | Hoarau |
| 2004/0181133 A1 | 9/2004 | Al-Ali et al. | | 2008/0076996 A1 | 3/2008 | Hoarau |
| 2004/0181134 A1 | 9/2004 | Baker, Jr. et al. | | 2008/0119700 A1 | 5/2008 | DeGould |
| 2004/0186358 A1 | 9/2004 | Chernow et al. | | 2008/0221413 A1 | 9/2008 | Hoarau |
| 2004/0199063 A1 | 10/2004 | O'Neil et al. | | | | |
| 2004/0204636 A1 | 10/2004 | Diab et al. | | | FOREIGN PATENT DOCUMENTS | |
| 2004/0204637 A1 | 10/2004 | Diab et al. | | DE | 19632361 | 2/1997 |
| 2004/0204638 A1 | 10/2004 | Diab et al. | | DE | 3703458 | 8/1998 |
| 2004/0204639 A1 | 10/2004 | Casciani et al. | | DE | 20318882 | 4/2004 |
| 2004/0204865 A1 | 10/2004 | Lee et al. | | EP | 0127947 | 5/1984 |
| 2004/0210146 A1 | 10/2004 | Diab et al. | | EP | 0204259 | 5/1986 |
| 2004/0215069 A1 | 10/2004 | Mannheimer | | EP | 0531631 | 3/1993 |
| 2004/0230106 A1 | 11/2004 | Schmitt et al. | | EP | 0724860 | 8/1996 |
| 2004/0230107 A1 | 11/2004 | Asada et al. | | EP | 1807001 | 7/2007 |
| 2004/0230108 A1 | 11/2004 | Melker et al. | | EP | 1830695 | 9/2007 |
| 2004/0236196 A1 | 11/2004 | Diab et al. | | EP | 1945099 | 7/2008 |
| 2004/0242980 A1 | 12/2004 | Kiani et al. | | FR | 2685865 | 1/1992 |
| 2004/0249252 A1 | 12/2004 | Fine et al. | | JP | 2111343 | 4/1990 |
| 2004/0257557 A1 | 12/2004 | Block et al. | | JP | 3116259 | 5/1991 |
| 2004/0260161 A1 | 12/2004 | Melker et al. | | JP | 3116260 | 5/1991 |

| | | |
|---|---|---|
| JP | 5049625 | 3/1993 |
| JP | 6014906 | 1/1994 |
| JP | 6269430 | 9/1994 |
| JP | 7001273 | 1/1995 |
| JP | 7236625 | 9/1995 |
| JP | 2000237170 | 9/2000 |
| JP | 2002224088 | 8/2002 |
| JP | 2003275192 | 9/2003 |
| JP | 2004089546 | 3/2004 |
| JP | 2004148070 | 5/2004 |
| JP | 2004159810 | 6/2004 |
| JP | 2004290544 | 10/2004 |
| JP | 2004329406 | 11/2004 |
| JP | 2004337605 | 12/2004 |
| JP | 2004344367 | 12/2004 |
| JP | 2004351107 | 12/2004 |
| JP | 2005110816 | 4/2005 |
| JP | 2007117641 | 5/2007 |
| JP | 2007135718 | 6/2007 |
| JP | 3944448 | 7/2007 |
| JP | 2007167183 | 7/2007 |
| JP | 2007167184 | 7/2007 |
| JP | 2007289462 | 11/2007 |
| JP | 2007289463 | 11/2007 |
| JP | 2007330708 | 12/2007 |
| JP | 4038280 | 1/2008 |
| WO | WO8909566 | 10/1989 |
| WO | WO9001293 | 2/1990 |
| WO | WO9111137 | 8/1991 |
| WO | WO9502358 | 1/1995 |
| WO | WO9736536 | 10/1997 |
| WO | WO9857577 | 12/1998 |
| WO | WO9947039 | 9/1999 |
| WO | WO0059374 | 10/2002 |
| WO | WO2005010567 | 2/2005 |
| WO | WO2005010568 | 2/2005 |
| WO | WO2006064399 | 6/2006 |
| WO | WO2008039391 | 4/2008 |

OTHER PUBLICATIONS

Nuhr, M., et al.: "Forehead SpO$_2$ monitoring compared to finger SpO$_2$ recording in emergency transport," *Anesthesia*, vol. 59, pp. 390-393 (2004).

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Faisst, Karin, et al.; "Intrapartum Reflectance Pulse Oximetry: Effects of Sensor Location and Fixation Duartion on Oxygen Saturation Readings," Journal of Clinical Monitoring, vol. 13, pp. 299-302 (1997).

Izumi, Akio, et al.; "Accuracy and Utility of a New Reflectance Pulse Oximeter for Fetal Monitoring During Labor," Journal of Clinical Monitoring, vol. 13, pp. 103-108 (1997).

"Smaller Product, Tighter Tolerances Pose Dispensing Challenges for Medical Device Manufacturer," Adhesives Age, pp. 40-41 (Oct. 1997).

Crilly, Paul B., et al.; "An Integrated Pulse Oximeter System for Telemedicine Applications," IEEE Instrumentation and Measurement Technology Conference, Ottawa, Canada; May 19-21, 1997; pp. 102-104.

DeKock, Marc; "Pulse Oximetry Probe Adhesive Disks: A Potential for Infant Aspiration," Anesthesiology, vol. 89, pp. 1603-1604 (1998).

Rhee, Sokwoo, et al.; "The Ring Sensor: a New Ambulatory Wearable Sensor for Twenty-Four Hour Patient Monitoring," Proceedings of the 20th annual International Conference of the IEEE Engineering in Medicine and Biology Society, vol. 20, No. 4, pp. 1906-1919 (Nov. 1, 1998).

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

Ferrell, T.L., et al.; "Medical Telesensors," SPIE, vol. 3253, pp. 193-198 (1998).

Rhee, Sokwoo et al.; "Design of a Artifact-Free Wearable Plethysmographic Sensor," Proceedings of the 21st Annual International Conference of the IEEE EMBS, Atlanta, GA. (Oct. 1999).

Yang, Boo-Ho, et al.; "Development of the ring sensor for healthcare automation," Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the 22nd Annual EMBS International Conference, Chicago, Illinois; Jul. 23-28, 2000; pp. 2796.

Schulz, Christian Eric; "Design of a Pulse Oximetry Sensor Housing Assembly," California State University Master's Thesis, UMI Dissertation Services, UMI No. 1401306, (May 2000) 63 pages.

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summ.

Gisiger, P.A., et al.; "OxiCarbo®, a single sensor for the non-invasive measurement of arterial oxygen saturation and CO2 partial pressure at the ear lobe," Sensor and Actuators, vol. B-76, pp. 527-530 (2001).

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Shaltis, Phillip, et al.; "Implementation and Validation of a Power-Efficient, High-Speed Modulation Design for Wireless Oxygen Saturation Measurement Systems," IEEE, pp. 193-194 (2002).

Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

Matsui, A., et al.; "Pulse Oximeter," Neonatal Care, vol. 16, No. 3, pp. 38-45 (2003) (Article in Japanese—contains English summary of article).

Asada, H. et al.; "Mobile Monitoring with Wearable Photoplethysmographic Biosensors," IEEE, pp. 28-40 (May/Jun. 2003).

Urquhart, C., et al.; "Ear probe pulse oximeters and neonates," Anaesthesia, vol. 60, p. 294 (2005).

\* cited by examiner

MEDICAL SENSOR

BACKGROUND

The present disclosure relates generally to medical sensors and, more particularly, to finger-type pulse oximeter sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Many types of medical sensors, such as optical sensors, are used to measure physiological characteristics of a patient. Typically, an optical sensor emits light into tissue, which then scatters through a portion of the tissue and is detected. Various characteristics of a patient can be determined from analyzing such detected light, such as oxygen saturation, pulse rate, tissue bilirubin, etc.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor that scatters light through a portion of the patient's tissue where blood perfuses the tissue and that photoelectrically senses the absorption of light in such tissue. The amount of light absorbed and/or scattered is then used to calculate the amount of blood constituent being measured.

The light transmitted through the tissue is selected to be of one or more wavelengths that are absorbed by the blood in an amount representative of the amount of the blood constituent present in the blood. The amount of transmitted light scattered through and/or absorbed by the tissue will vary in accordance with the changing amount of blood constituent in the tissue. For measuring blood oxygen level, such sensors have typically been provided with a light source that is adapted to generate light of at least two different wavelengths, in accordance with known techniques for measuring blood oxygen saturation.

Known non-invasive sensors include devices that are secured to a portion of the body, such as a finger, an ear, or the scalp. In animals and humans, the tissue of these body portions is perfused with blood and the tissue surface is readily accessible to the sensor. However, sensors are generally designed for the body part to which they attach. For example, a sensor configured to attach to a finger could produce inaccurate measurements if it was attached to the scalp.

DETAILED DESCRIPTION

One or more embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Some embodiments are directed toward configuring a medical finger sensor such that it may not be attached to a patient's body at any location other than the finger. For example, a sensor body containing an emitter and a detector may be attached to a ring. When a patient or clinician places the ring on the patient's finger, the emitter and detector are communicatively coupled to the patient's finger. However, because the sensor body is attached to the ring, the sensor body may not be placed flat on the patient's forehead, for example, thus ensuring that the finger sensor is properly placed on the patient's finger.

Figure 1:
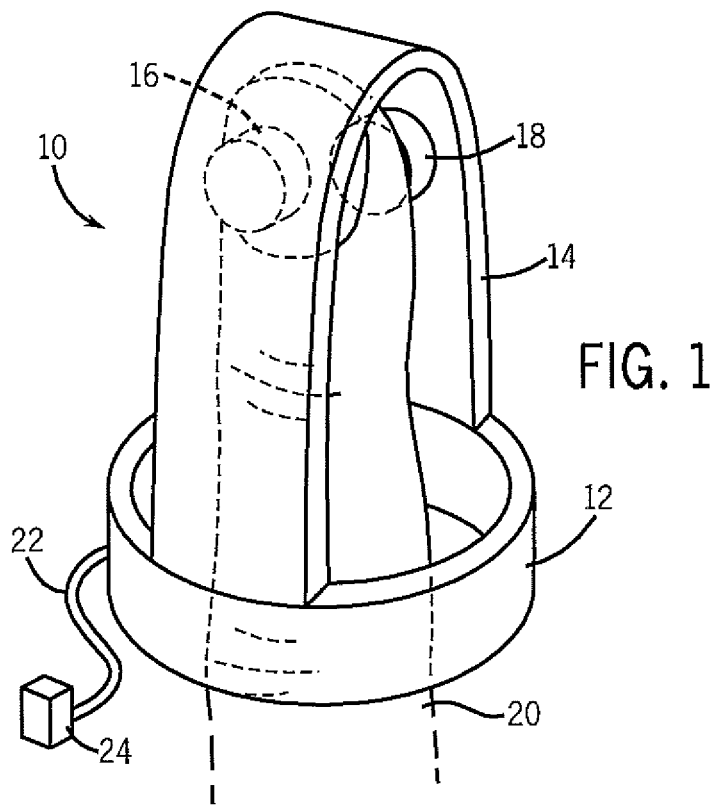
FIG. 1 is an example of a medical finger sensor, in accordance with an embodiment of the present disclosure.

Typical medical finger sensors comprise a flat strip configured to wrap around the distal end of the patient's finger. However, as discussed above, this flat strip may be placed on portions of the patient's body other than the finger. To prevent such misuse, a ring may be attached to this flat strip, limiting application of the medical finger sensor to the patient's finger. FIG. 1 is a drawing of a medical finger sensor 10 according to an embodiment. As illustrated, a ring 12 is attached to a sensor body 14, containing an emitter 16 and a detector 18. In this embodiment, placing the ring 12 on a patient's finger 20 causes the emitter 16 and the detector 18 to contact the finger 20. The emitter 16 and the detector 18 may be components of a transmission-type pulse oximetry sensor. Furthermore, as discussed below, the pulse oximetry sensor may be connected to a patient monitor via the external sensor cable 22 and the sensor connector 24.

According to an embodiment, transmission-type sensors may include an emitter 16 and a detector 18 that are typically placed on opposite sides of the sensor site. If the sensor site is a fingertip, for example, a medical finger sensor 10 may be positioned over the patient's fingertip such that the emitter 16 and detector 18 lie on opposite sides of the patient's nail bed.

In other words, the medical finger sensor 10 may be positioned so the emitter 16 is located on the patient's fingernail and the detector 18 is located opposite the emitter 16 on the patient's finger pad. During operation, the emitter 16 shines one or more wavelengths of light through the patient's fingertip, and the light received by the detector 18 is processed to determine various physiological characteristics of the patient. In each of the embodiments discussed herein, it should be understood that the locations of the emitter 16 and detector 18 may be interchanged. For example, the detector 18 may be located at the top of the finger and emitter 16 may be located underneath the finger. In either arrangement, the medical finger sensor 10 will perform in substantially the same manner.

The emitter 16 and the detector 18 may be of any suitable type. For example, the emitter 16 may be one or more light emitting diodes adapted to transmit one or more wavelengths of light in the red to infrared range, and the detector 18 may be one or more photodetectors selected to receive light in the range or ranges emitted from the emitter 16. Alternatively, the emitter 16 may also be a laser diode or a vertical cavity surface-emitting laser (VCSEL). Emitter 16 and detector 18 may also include optical fiber elements. An emitter 16 may include a broadband or "white light" source, in which case the detector 18 could include any variety of elements for selecting specific wavelengths, such as reflective or refractive elements or interferometers. These kinds of emitters and detectors would typically be coupled to the rigid or rigidified sensor via fiber optics. Alternatively, the medical finger sensor 10 may sense light detected from the tissue at a different wavelength from the light emitted into the tissue. Such sensors may be adapted to sense fluorescence, phosphorescence, Raman scattering, Rayleigh scattering and multi-photon events or photoacoustic events. Similarly, in other applications, a tissue water fraction (or other tissue constituent related metric) or a concentration of one or more biochemical components in an aqueous environment may be measured using two or more wavelengths of light. In certain embodiments, these wavelengths may be infrared wavelengths between about 1,000 nm to about 2,500 nm.

It should be understood that, as used herein, the term "light" may refer to one or more of ultrasound, radio, microwave, millimeter wave, infrared, visible, ultraviolet gamma ray or X-ray, and/or electromagnetic radiation, and may also include any wavelength within the radio, microwave, infrared, visible, ultraviolet, or X-ray spectra, and that any suitable wavelength of light may be appropriate for use with the present techniques.

Returning to FIG. 1, the illustrated embodiment shows a ring 12 with a fixed diameter. The ring 12 in this embodiment forms a continuous loop around the patient's finger 20 and may not be adjusted. The diameter of the ring 12 may be sufficient to accommodate fingers of varying girth. The ring 12 may be composed of a rigid material, such as metal or hard plastic, or a flexible material, such as cloth, paper or soft plastic.

Tightly securing the ring 12 to the patient's finger 20 may facilitate improved contact between the finger 20 and the sensor components (emitter 16 and detector 18). Therefore, the ring 12 may be composed of an elastic material which may expand to fit the patient's finger 20. The unexpanded diameter of the ring 12 may be small enough to securely attach to a thin finger, while allowing for expansion sufficient to accommodate a thick finger.

Figure 2:
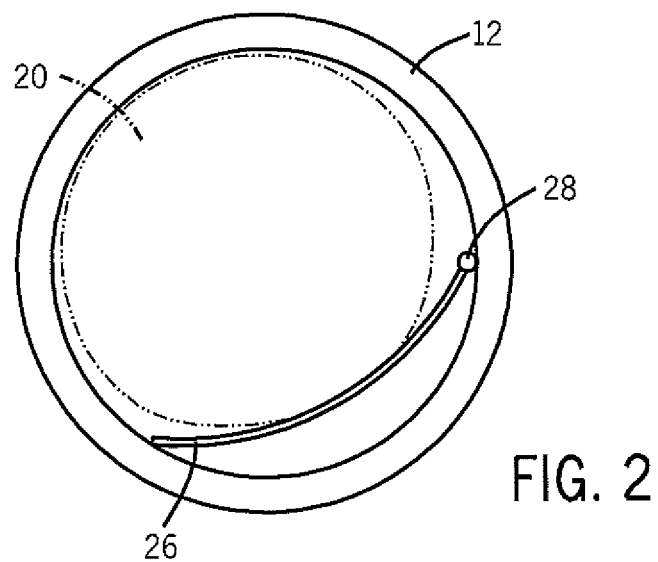
FIG. 2 is a bottom view of a rigid adjustable ring utilizing a leaf spring mechanism that may be used with the medical finger sensor of FIG. 1.
Figure 3:
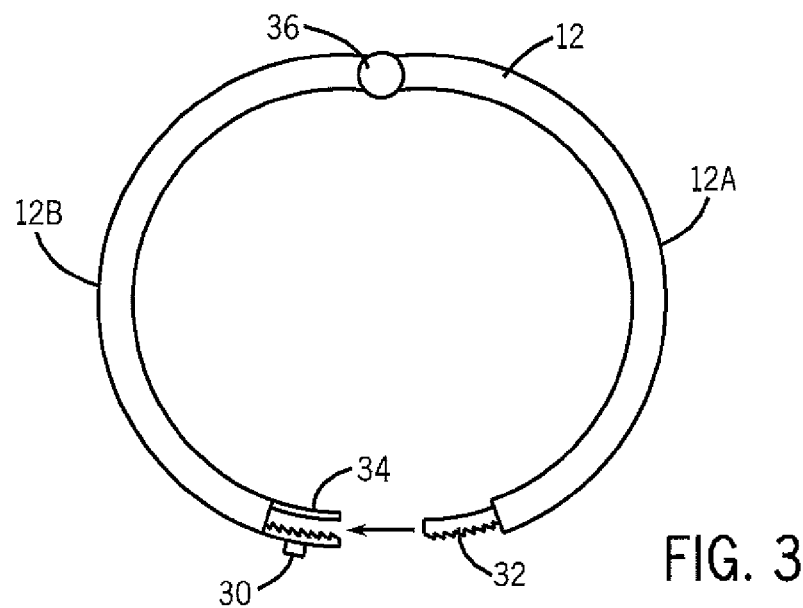
FIG. 3 is a bottom view of a rigid adjustable ring utilizing a ratcheting mechanism that may be used with the medical finger sensor of FIG. 1.

According to an embodiment, other ring configurations may also serve to tightly secure the ring 12 to the patient's finger 20. For example, FIGS. 2 and 3 present various embodiments in which the ring 12 is constructed of a rigid material and its diameter is adjustable. FIG. 2 illustrates a leaf spring mechanism that may automatically adjust the diameter of the ring 12 based on the thickness of the patient's finger. In this embodiment, a semicircular spring 26 may be attached to an inner surface of the rigid ring 12 at one point 28. As the patient's finger enters the ring, the semicircular spring 26 may compress, providing tension around the patient's finger. However, excessive tension may reduce blood flow to the finger, leading to inaccurate sensor readings. Therefore, the spring force may be adjusted to provide tension around the patient's finger without reducing circulation.

Similarly, FIG. 3 demonstrates another embodiment of a rigid adjustable ring. In this embodiment, a ratcheting mechanism may be employed to facilitate manual adjustment of the ring diameter. Applying pressure to a ratchet release mechanism 30 permits a sizing section 32 to be incrementally inserted into or removed from a ring opening 34. As the size of the ring changes, each ring segment 12A and 12B rotates about a hinge 36 located opposite the ratchet release mechanism along the circumference of the ring 12. In this manner, the ring 12 may be adjusted by small increments to properly fit a patient's finger. Furthermore, the hinge 36 may be configured to limit the angle of expansion such that the sizing section 32 may not be completely removed from the ring opening 34. This hinge configuration may ensure that the ring 12 maintains a continuous loop.

According to an embodiment, a ring constructed of a flexible material may be adjustable as well. For example, the ring 12 depicted in FIG. 4 may include a low-stretch, i.e., generally inelastic, segment 38 sized to fit around a patient's finger, and a generally elastic band 40 that may be coupled to the low-stretch segment 38. The generally elastic band 40 may be elastic along substantially its entire length, or it may include an elastic portion and an inelastic portion. In this embodiment, the elastic band 40 has a loose end 42 and an attached end 44, where the elastic band 40 is attached at its attached end 44 with the low-stretch segment 38. The elastic band 40 is threaded through a guide band 46 of the low-stretch segment 38, which functions to prevent slippage of the elastic band 40. In this configuration, the diameter of the flexible ring 12 may be adjusted to fit the patient's finger 20.

According to an embodiment, when securing an adjustable ring 12 to the patient's finger 20, selecting a proper tension is important to producing accurate medical measurements. For example, if the tension is too low, the emitter 16 and the detector 18 may not adequately contact the patient's finger 20. If the tension is too high, blood flow to the finger may be reduced, leading to inaccurate sensor readings. To facilitate proper ring adjustment, the ring 12 may indicate when it has been secured with the appropriate tension. Specifically, the elastic band 40 may include tension arrows 48 that align with a tension indicator zone 50 on the low-stretch segment 38 when the elastic band 40 is in a stretched state. In this embodiment, the opposite face of the loose end 42 of the elastic band 40 has hook and loop fasteners 52 which may couple to the low-stretch segment 38 to affix to the ring 12 around the patient's finger 20 and maintain the ring 12 at the desired tension. Hence, when the low-stretch segment 38 has been placed about the patient's finger 20 and secured in the proper range with the tension arrows 48 aligned in the tension indicator zone 50, the ring 12 should be adequately secured to the patient's finger 20 in a manner that will facilitate proper sensor readings from the sensor described above.

Figure 4:
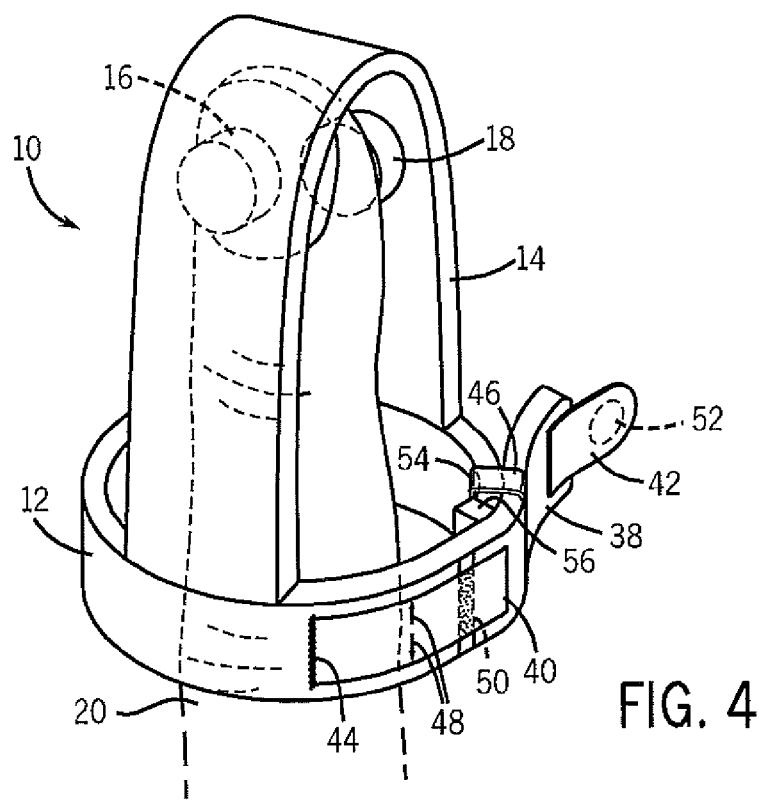
FIG. 4 is a drawing of an adjustable ring with a tension indicator that may be used with the medical finger sensor of FIG. 1.
Figure 5:
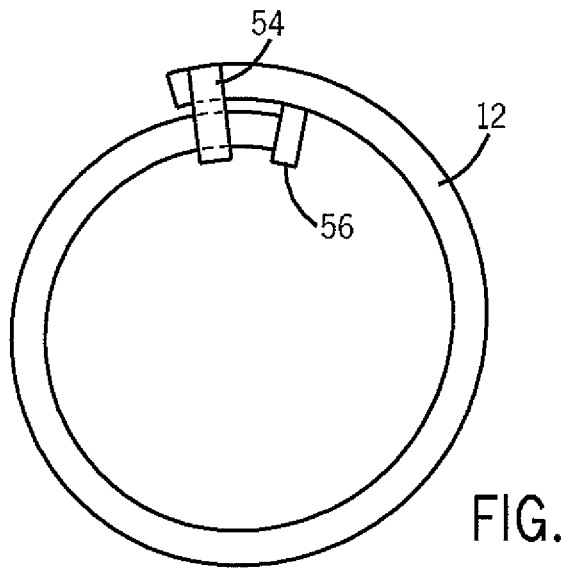
FIG. 5 is a bottom view of an adjustable ring with an expansion limiter that may be used with the adjustable ring of FIG. 4.

As previously discussed, the finger sensor should not be reconfigured such that it may be applied to another part of a patient's body. To prevent such a reconfiguration, the ring 12 may be adapted such that its diameter is adjustable, but the ring 12 maintains a continuous loop even when not secured to the patient's finger 20. FIGS. 4 and 5 illustrate how this functionality may be accomplished in an embodiment. A retention band 54 may be attached to the guide band 46 along an outer surface of the ring 12. The low-stretch segment 38 may then pass through the retention band 54. In addition, an expansion limiter 56 may be attached to an end of the low-stretch segment 38 opposite the guide band 46. The expansion limiter 56 may be configured such that it is incapable of passing through the retention band 54. Therefore, in this embodiment the ring 12 may maintain a continuous loop even when the hook and loop fasteners 52 are uncoupled from the low-stretch segment 38. The expansion limiter 56 may take any suitable form so long as it prevents the ring 12 from being separated and opened. For example, the expansion limiter 56 may comprise a solid attachment to the end of the low-stretch segment 38, or it may comprises a section of the low-stretch segment 38 of greater thickness.

Figure 6:
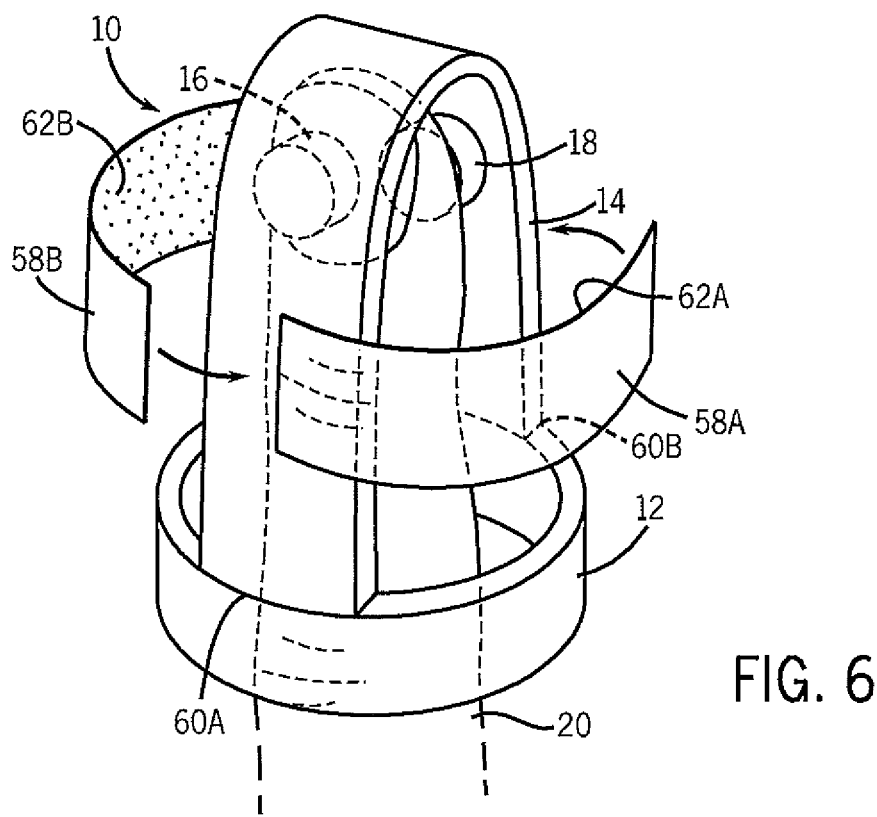
FIG. 6 is a drawing of a strip-type sensor body with two securing flaps that may be used with the medical finger sensor of FIG. 1.

According to embodiments, various sensor body configurations may be employed to couple the emitter 16 and the detector 18 to the patient's finger 20. One such configuration may include the strip-type sensor body 14 depicted in FIG. 6. As illustrated, the sensor body 14 is connected to the ring 12 at two attachment points 60A and 60B. The attachment points 60 may be positioned opposite each other along the circumference of the ring 12. In the present embodiment, the securing mechanism comprises two flaps 58A and 58B. The flaps 58 may be coated on one side with a layer of pressure sensitive adhesive 62. In this embodiment, an adhesive layer 62A is affixed to a front side of flap 58A, while an adhesive layer 62B is affixed to a back side of flap 58B. In this configuration, when the flaps 58 are wrapped around the patient's finger 20 in a counter-clockwise direction, the flaps 58 are adhesively coupled to the sensor body 14 and the patient's finger 20, serving to secure the sensor body 14 to the finger 20. The resulting contact between the finger 20 and the sensor body 14 may ensure a proper coupling of the finger 20 to the emitter 16 and the detector 18.

To further secure the sensor body 14 to the patient's finger 20, an adhesive layer may be affixed to an inner surface of the sensor body 14. In this embodiment, the sensor body 14 may adhere to the finger 20 upon contact. Similar to the previous embodiment, this adhesion may provide effective coupling between the finger 20 and the sensor components (emitter 16 and detector 18). The adhesive layer affixed to the sensor body 14 may be the sole securing mechanism, or it may be combined with the flaps 58 described above.

Figure 7:
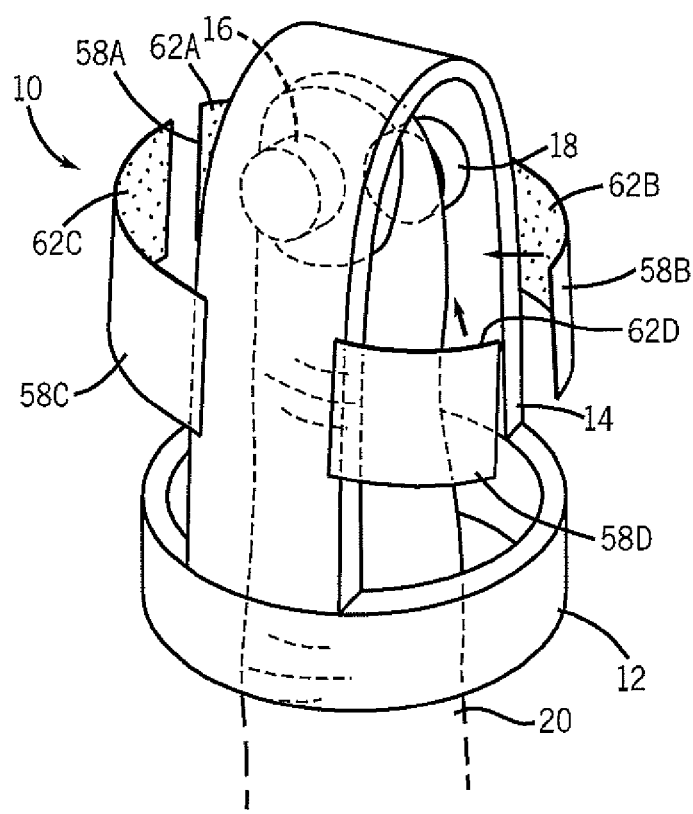
FIG. 7 is a perspective view of a strip-type sensor body with four securing flaps that may be used with the medical finger sensor of FIG. 1.

Another embodiment of the securing mechanism may employ four flaps 58 to secure the sensor body 14 to the patient's finger 20. In this embodiment, as shown in FIG. 7, adhesive layers 62A and 62B may be affixed to a bottom surface of flaps 58A and 58B, respectively. Similarly, adhesive layers 62C and 62D may be affixed to a top surface of flaps 58C and 58D, respectively. When flaps 58A and 58C are placed in contact with each other, they may adhere to one another, forming a bond between the two flaps (58A and 58C). Correspondingly, flaps 58B and 58D may form a similar bond upon contact. The combination of adhering flap 58A to flap 58C and flap 58B to flap 58D may serve to secure the sensor body 14 to the patient's finger 20. In addition, a layer of adhesive may be affixed to an inner surface of the sensor body 14, further securing the sensor body 14 to the patient's finger 20.

Figure 8:
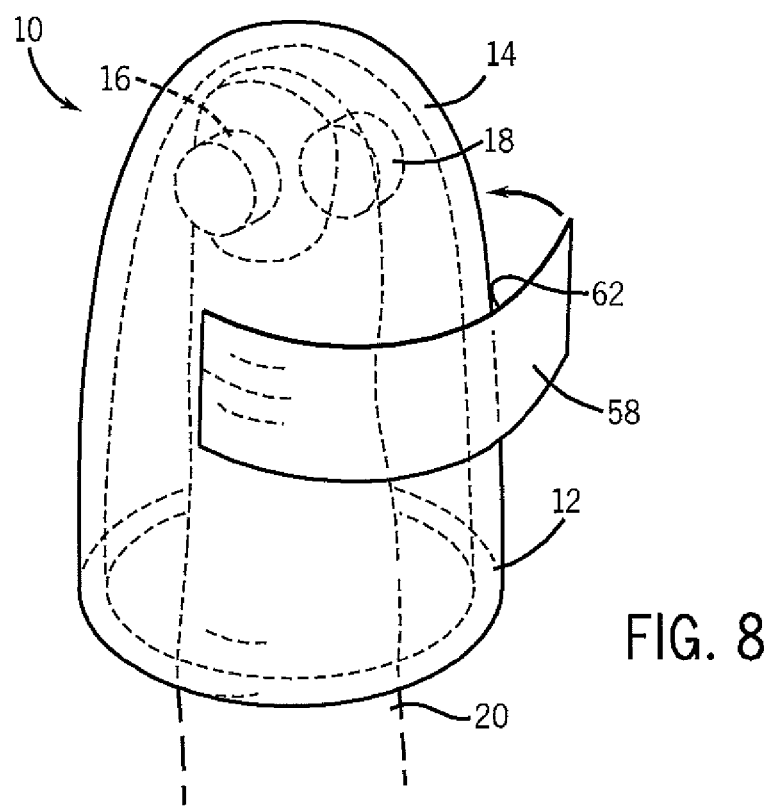
FIG. 8 is a drawing of a hood-type sensor body with one securing flap that may be used with the medical finger sensor of FIG. 1.

In certain situations ambient light may interfere with the effectiveness of the detector 18. For example, if a patient has sensitive skin or is allergic to the adhesive described above, a medical finger sensor 10 without adhesives, either on the sensor body 14 or the flaps 58, may be employed. However, without adhesives to secure the sensor body 14 to the patient's finger 20, a gap may form between the detector 18 and the finger 20. This gap may allow ambient light to enter the detector 18, interfering with its ability to measure light from the emitter 16. To combat ambient light, a substantially opaque hood-type sensor body 14 may be placed around the finger 20. For example, FIG. 8 presents an embodiment in which the sensor body 14 forms a hood around the distal end of the patient's finger 20. The hood-type sensor body 14 may be attached to the ring 12 along the ring's circumference, extending 180 degrees or more around the ring 12. The sensor body 14 may be configured to enclose all or a portion of the distal end of the finger 20. In this embodiment, a single flap 58 may be coupled to the sensor body 14 such that when secured, the flap 58 and the hood 14 form a complete loop around the finger 20. The flap 58 may also have a layer of adhesive 62 affixed to a front surface. In this configuration, when the flap 58 is wrapped around the finger 20 in a counter-clockwise direction, the flap 58 may secure the sensor body 14 to the finger 20, ensuring contract between the finger 20 and the sensor components (emitter 16 and detector 18). Furthermore, an adhesive may be affixed to an inner surface of the hood-type sensor body 14, further securing the finger 20 to the sensor body 14.

Figure 9:
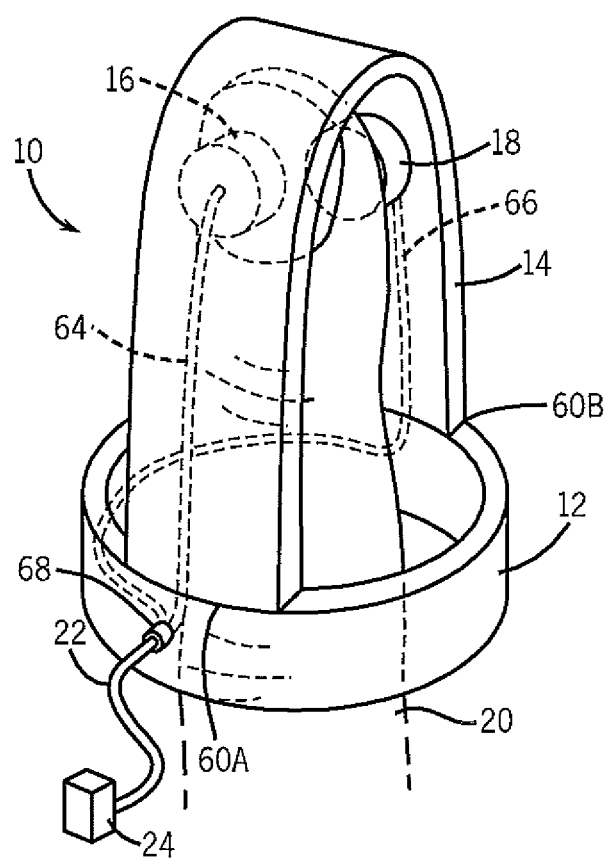
FIG. 9 is a drawing of the medical finger sensor of FIG. 1 showing the path of internal sensor conductors.

As discussed above, the medical finger sensor 10 should not be reconfigured such that the sensor body 14 may be placed on a portion of a patient's body other than the finger 20. For example, if the sensor body 14 was physically removed from the ring 12, the sensor body 14 may be attached to a patient's scalp. Such a misuse of the sensor body 14 could yield inaccurate measurements of medical parameters. One embodiment which may prevent the sensor body 14 from being removed from the ring 12 is illustrated in FIG. 9. In this embodiment, internal conductors 64 and 66 connect the emitter 16 and the detector 18 to the sensor cable junction 68. The emitter conductor 64 may originate at the emitter 16 and extend down the sensor body 14 through the connection point 60A to the ring 12. The emitter conductor 64 may then traverse the circumference of the ring 12 to the sensor cable junction 68. In the sensor cable junction 68, the emitter conductor 64 may be coupled to the detector conductor 66 and the external sensor cable 22. Similarly, the path of the detector conductor 66 may begin at the detector 18 and pass down the sensor body 14. The detector conductor 66 may then pass through the connection point 60B and around the circumference of the ring 12 to the sensor cable junction 68. At the sensor cable junction 68, the detector conductor 66 may form an electrical connection with both the emitter conductor 64 and the external sensor cable 22. In this embodiment, separation of the sensor body 14 from the ring 12 at either connection point 60A or 60B will sever the emitter conductor 64 and/or the detector conductor 66. Without a proper connection to both the emitter 16 and the detector 18, the medical finger sensor 10 will not function.

According to an embodiment, separating the sensor body 14 from the ring 12 will only sever the internal conductors 64 and 66 if the conductors are physically coupled to the medical finger sensor 10. In other embodiments, for example, if the ring 12 or sensor body 14 is composed of multiple layers of soft plastic, the internal conductors 64 and 66 may pass between two of the layers. Similarly, if the ring 12 or sensor body 14 is composed of fabric, the internal conductors 64 and 66 may be sewn into the fabric. If the ring 12 is composed of a rigid material such as hard plastic or metal, the internal conductors 64 and 66 may pass through holes in the ring 12 located at each connection point 60. In these configurations, the sensor body 14 could not be removed from the ring 12 without severing at least one of the internal conductors 64 or 66.

Figure 10:
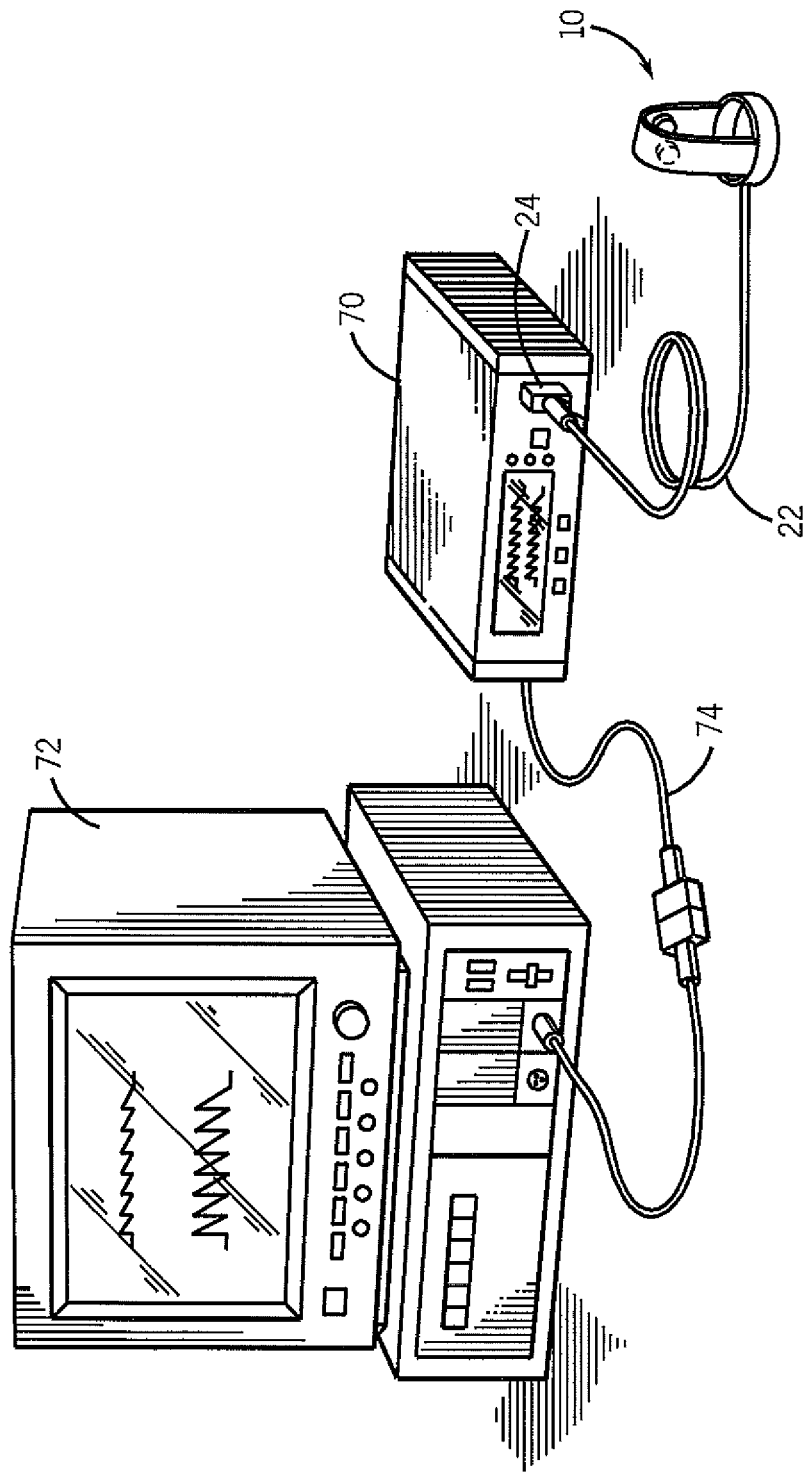
FIG. 10 is a patient monitoring system coupled to a multi-parameter patient monitor and the medical finger sensor of FIG. 1.

According to an embodiment, it should be appreciated that the medical finger sensor 10 is designed for use with a patient monitoring system. For example, referring now to FIG. 10, the medical finger sensor 10 as depicted in FIG. 1 may be used in conjunction with a patient monitor 70. In an embodiment an external sensor cable 22 connects the medical finger sensor 10 to the patient monitor 70 via a sensor connector 24. The medical finger sensor 10 and/or external sensor cable 22 may include or incorporate one or more integrated circuit or electrical devices, such as a memory processor chip, that may facilitate or enhance communication between the medical finger sensor 10 and the patient monitor 70. Similarly, the external sensor cable 22 may be an adaptor cable, with or without an integrated circuit or electrical device, for facilitating communication between the medical finger sensor 10 and various types of monitors, including different versions of the patient monitor 70 or other physiological monitors. In other embodiments, the medical finger sensor 10 and the patient monitor 70 may communicate via wireless means, such as using radio frequency, infrared or optical signals. In such embodiments, a transmission device may be connected to the medical finger sensor 10 to facilitate wireless transmission between the medical finger sensor 10 and patient monitor 70. The external sensor cable 22 (or a corresponding wireless connection) may typically be used to transmit control or timing signals from the patient monitor 70 to the medical finger sensor 10 and/or to transmit acquired data from the medical finger sensor 10 to the patient monitor 70. In other embodiments, the external sensor cable 22 may be an optical fiber that enables optical signals to be transmitted between the patient monitor 70 and the medical finger sensor 10.

In one embodiment, the patient monitor 70 may be a suitable pulse oximeter, such as those available from Nellcor Puritan Bennett L.L.C. In other embodiments, the patient monitor 70 may be a monitor suitable for measuring tissue water fractions, or other body fluid related metrics, using spectrophotometric or other techniques. Furthermore, the patient monitor 70 may be a multipurpose monitor suitable for performing pulse oximetry and measurement of tissue water fraction, or other combinations of physiological and/or biochemical monitoring processes, using data acquired via the medical finger sensor 10 and/or other sensors. Moreover, to upgrade conventional monitoring functions provided by the system, the patient monitor 70 may be coupled to a multi-parameter patient monitor 72 via a monitor cable 74 connected to a sensor input port and/or a cable connected to a digital communication port.

While the disclosure may be susceptible to various modifications and alternative forms, specific embodiments have been shown by way of example in the drawings and have been described in detail herein. However, it should be understood that the disclosure is not intended to be limited to the particular forms provided. Rather, the disclosure is to cover all modifications, equivalents, and alternatives falling within the spirit and scope of the disclosure as defined by the following appended claims. Indeed, the present disclosed methods may not only be applied to transmission type sensors for use in pulse oximetry, but also to other sensor designs.

What is claimed is:

1. A sensor comprising:
   a ring configured to be placed on a patient's finger and to maintain a continuous loop when removed from the patient's finger and configured to maintain the continuous loop when adjusting the size of the ring, wherein the ring comprises an inelastic segment configured to be placed around the patient's finger, and an elastic segment coupled to the inelastic segment, the elastic segment having a fastener to secure the ring to the patient's finger;
   a sensor body being integrally coupled to the ring and having a substantially closed end and a substantially open end, the substantially open end being coupled to the ring, and the substantially closed end configured to at least partially enclose a distal end of the patient's finger when the ring is placed on the patient's finger;
   a securing mechanism coupled to the sensor body, the securing mechanism configured to secure the sensor body to the finger; and
   a sensor disposed on the sensor body, the sensor configured to communicatively couple to the patient's finger.

2. The sensor of claim 1, wherein the inelastic segment comprises at least one indicator and the elastic segment comprises at least one tension indicator zone configured to align with the indicator to indicate whether the ring has been secured to a patient's finger at an appropriate tension.

3. The sensor of claim 1, wherein the sensor comprises a pulse oximetry sensor.

4. The sensor of claim 3, wherein the sensor comprises a transmission-type pulse oximetry sensor.

5. The sensor of claim 3, wherein the sensor comprises a reflectance-type pulse oximetry sensor.

6. The sensor of claim 1, wherein the sensor is configured to be disabled if the sensor body is at least partially separated from the ring.

7. A pulse oximetry system comprising:
   a pulse oximetry monitor; and
   a pulse oximetry sensor operatively coupled to the pulse oximetry monitor, the pulse oximetry sensor comprising:
   a ring configured to be placed on a patient's finger and to maintain a continuous loop when removed from the patient's finger and configured to maintain the continuous loop when adjusting the size of the ring, wherein the ring comprises an inelastic segment configured to be placed around the patient's finger, and an elastic segment coupled to the inelastic segment, the elastic segment having a fastener to secure the ring to the patient's finger;
   a sensor body being integrally coupled to the ring and having a substantially closed end and a substantially open end, the substantially open end being coupled to the ring, and the substantially closed end being configured to at least partially enclose a distal end of the patient's finger when the ring is placed on the patient's finger;
   a securing mechanism coupled to the sensor body, the securing mechanism being configured to secure the sensor body to the finger; and
   a sensor disposed on the sensor body, the sensor being configured to communicatively couple to the patient's finger.

8. The system of claim 7, wherein the inelastic segment comprises at least one indicator and the elastic segment comprises at least one tension indicator zone configured to align with the indicator to indicate whether the ring has been secured to a patient's finger at an appropriate tension.

9. The system of claim 7, wherein the sensor comprises a transmission-type pulse oximetry sensor.

10. The system of claim 7, wherein the sensor is configured to be disabled if the sensor body is at least partially separated from the ring.

11. The system of claim 7, wherein the sensor comprises a reflectance-type pulse oximetry sensor.

* * * * *